(12) United States Patent
Chen et al.

(10) Patent No.: US 6,869,615 B2
(45) Date of Patent: *Mar. 22, 2005

(54) PHARMACEUTICAL FORMULATIONS CONTAINING A NON-STEROIDAL ANTIINFLAMMATORY DRUG AND A PROTON PUMP INHIBITOR

(75) Inventors: Chih-Ming Chen, Davie, FL (US); Unchalee Kositprapa, Davie, FL (US)

(73) Assignee: Andrx Labs LLC, Davie, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/282,820

(22) Filed: Oct. 28, 2002

(65) Prior Publication Data

US 2003/0129235 A1 Jul. 10, 2003

Related U.S. Application Data (63) Continuation of application No. 09/659,222, filed on Sep. 11, 2000, now Pat. No. 6,544,556.

(51) Int. Cl.[7] .............................. A61K 9/20; A61K 9/22; A61K 9/26; A61K 9/28; A61K 9/54
(52) U.S. Cl. ........................ 424/469; 424/451; 424/452; 424/457; 424/458; 424/465; 424/468; 424/489; 424/470; 424/474; 424/490
(58) Field of Search ................................. 424/489, 490, 424/469, 451, 452, 457, 458, 464, 465, 470, 472, 468, 474, 484, 455, 456, 480, 481, 482, 493, 494, 495, 497, 496, 477

(56) References Cited

U.S. PATENT DOCUMENTS

| | | | |
|---|---|---|---|
| 3,161,654 A | 12/1964 | Shen | 548/500 |
| 3,228,831 A | 1/1966 | Nicholson et al. | 514/568 |
| 3,385,886 A | 5/1968 | Nicholson et al. | 562/492 |

(List continued on next page.)

FOREIGN PATENT DOCUMENTS

| | | | |
|---|---|---|---|
| EP | 0005129 | 4/1979 | C07D/403/12 |
| EP | 0166287 | 6/1985 | C07D/401/12 |
| EP | 0174726 | 7/1985 | C07D/401/12 |
| EP | 0295603 | 6/1988 | C07D/401/12 |
| EP | 0519365 | 6/1992 | A61K/9/20 |
| GB | 2163747 | 3/1986 | C07D/235/28 |
| WO | 9427988 | 12/1994 | C07D/401/12 |
| WO | 9501977 | 1/1995 | C07D/401/12 |
| WO | 9725064 | 7/1997 | A61K/45/06 |

OTHER PUBLICATIONS

Hawkey, Chrisotpher J., et al., *Omeprazole Compared with Misoprostol for Ulcers Associated with Nonseriodal Antiinflammatory Drugs*, New England Journal of Medicine (Mar. 12, 1988), 338:727–734.

*Primary Examiner*—James M. Spear
(74) *Attorney, Agent, or Firm*—Davidson, Davidson & Kappel, LLC

(57) ABSTRACT

An oral solid dosage form includes a therapeutically effective amount of an NSAID and a proton pump inhibitor in an amount effective to inhibit or prevent gastrointestinal side effects normally associated with the NSAID. Also disclosed is a method of treating a human patient in need of antiinflammatory, analgesic and/or antipyretic therapy, comprising orally administering to the patient an oral pharmaceutical dosage form which includes a therapeutically effective amount of an NSAID and an amount of a proton pump inhibitor effective to substantially inhibit gastrointestinal side effects of the NSAID. The invention is further related to a method of prophylactically treating a human patient who is on a therapy known to have significant gastrointestinal side effects or is about to begin such a therapy, via concurrent administration of an NSAID and a proton pump inhibitor in a combination (single) oral dosage form.

26 Claims, 4 Drawing Sheets

U.S. PATENT DOCUMENTS

| | | | |
|---|---|---|---|
| 3,558,690 A | 1/1971 | Sallman et al. | 560/47 |
| 3,591,584 A | 7/1971 | Lombardino | 544/49 |
| 3,600,437 A | 8/1971 | Marshall | 562/465 |
| 3,766,263 A | 10/1973 | Godfrey | 562/465 |
| 3,843,681 A | 10/1974 | Demerson et al. | 548/432 |
| 3,845,215 A | 10/1974 | Godfrey | 514/557 |
| 3,904,682 A | 9/1975 | Fried et al. | 562/466 |
| 4,009,197 A | 2/1977 | Fried et al. | 560/56 |
| 4,045,563 A | 8/1977 | Berntsson et al. | 514/338 |
| 4,255,431 A | 3/1981 | Junggren et al. | 514/338 |
| 4,359,465 A | 11/1982 | Ruwart | 514/314 |
| 4,472,409 A | 9/1984 | Senn-Bilfinger | 514/338 |
| 4,508,905 A | 4/1985 | Junggren et al. | 546/273.7 |
| 4,628,098 A | 12/1986 | Nohara et al. | 546/273.7 |
| 4,738,975 A | 4/1988 | Nohara et al. | 514/338 |
| 4,786,505 A | 11/1988 | Lovgren et al. | 424/468 |
| 4,853,230 A | 8/1989 | Lovgren et al. | 424/466 |
| 5,006,547 A | 4/1991 | Loose | 514/414 |
| 5,008,283 A | 4/1991 | Blackburn et al. | 514/414 |
| 5,039,806 A | 8/1991 | Brandstram et al. | 546/271 |
| 5,045,321 A | 9/1991 | Makino et al. | 424/475 |
| 5,045,552 A | 9/1991 | Souda et al. | 514/338 |
| 5,068,458 A | 11/1991 | Dales et al. | 568/634 |
| 5,204,118 A | 4/1993 | Goldman et al. | 424/489 |
| 5,312,824 A | 5/1994 | Sohda et al. | 514/338 |
| 5,417,980 A | 5/1995 | Goldman et al. | 424/464 |
| 5,510,382 A | 4/1996 | Stjernschantz et al. | 514/530 |
| 5,629,305 A | 5/1997 | Eek et al. | 514/199 |
| 5,708,017 A | 1/1998 | Dave et al. | 514/393 |
| 5,798,120 A | 8/1998 | Tomohisa et al. | 424/482 |
| 5,817,338 A | 10/1998 | Bergstrand et al. | 424/468 |
| 5,877,192 A | 3/1999 | Lindberg et al. | 514/338 |
| 6,365,184 B1 * | 4/2002 | Depui et al. | 424/469 |
| 6,544,556 B1 * | 4/2003 | Chen et al. | 424/469 |
| 6,613,354 B2 * | 9/2003 | Depui et al. | 424/458 |

* cited by examiner

PHARMACEUTICAL FORMULATIONS CONTAINING A NON-STEROIDAL ANTIINFLAMMATORY DRUG AND A PROTON PUMP INHIBITOR

This application is a continuation of U.S. application Ser. No. 09/659,222, filed on Sep. 11, 2000 now U.S. Pat. No. 6,544,556, the disclosure of which is hereby incorporated by reference in its entirety.

FIELD OF THE INVENTION

The present invention is related to the combination of a non-steroidal antiinflammatory drug ("NSAID") or one of its single enantiomers or salt of the NSAID, and a proton pump inhibitor or one of its single enantiomers, or an alkaline salt of the proton pump inhibitor or one of its single enantiomers, in a single oral pharmaceutical dosage form.

BACKGROUND

Although NSAIDs are often used for their antiinflammatory, analgesic, and/or antipyretic effects, it is well known that NSAIDs have the potential to cause gastrointestinal (GI) bleeding through a variety of mechanisms related to their topical and systemic effects. The GI bleeding may depend on the length of the treatment and on the particular drug. This problem is important in cases where the therapy must be continued for a long period of time. For example, osteoarthritis and rheumatoid arthritis in the elderly is often treated with long-term NSAID therapy, as chronic treatment is needed to control pain and inflammation and to improve quality of life.

Additionally it is well known that because of their side-effects on the GI tract, NSAIDs are invariably administered after meals or, generally, when the stomach is not empty. This pharmacological principle is confirmed by the recommendations found in the labeling of these medications. Patients who have an ulcer or who are susceptible to developing ulcers are commonly advised to avoid taking NSAIDs for pain, inflammation, and/or fever.

Other measures which can be taken to decrease GI side affects associated with NSAID therapy is to coadminister an $H_2$ blocker e.g. ranitidine, or a prostaglandin analogue, e.g. misoprostol, with the NSAID. In fact, a combination tablet containing diclofenac sodium and misoprostol (Arthrotec®, Pharmacia Corp.) has had FDA approval since 1988.

There is a continuing need for analgesic medications able to provide high efficacy pain relief while reducing the possibility of undesirable effects. Non-steroidal anti-inflammatory drugs, including compounds such as ibuprofen, ketoprofen and diclofenac, have anti-inflammatory actions and are effective on pain associated with the release of prostaglandins and other mediators of inflammation. For example, diclofenac and pharmaceutically acceptable salts thereof, e.g. diclofenac sodium, are considered to be extremely potent and effective as an analgesic and anti-inflammatory agent. Diclofenac is approved in the United States for the long-term symptomatic treatment of rheumatoid arthritis, osteoarthritis and ankylosing spondylitis. It is also considered to be useful for the short-term treatment of acute musculoskeletal injury, acute shoulder pain, postoperative pain and dysmenorrhea. However, NSAIDs such as diclofenac produce side effects in about 20% of patients that require cessation of medication. Side effects include, for example, gastrointestinal bleeding and the abnormal elevation of liver enzymes.

Non-steroidal anti-inflammatory drugs (NSAIDs) exert most of their anti-inflammatory, analgesic and antipyretic activity and inhibit hormone-induced uterine contractions and certain types of cancer growth through inhibition of prostaglandin G/H synthase, also known as cyclooxygenase. Inhibition of COX-1 causes a number of side effects including inhibition of platelet aggregation associated with disorders of coagulation, and gastrointestinal side effects with the possibility of ulcerations and of hemorrhage. It is believed that the gastrointestinal side effects are due to a decrease in the biosynthesis of prostaglandins which are cytoprotective of the gastric mucosa.

A high incidence of side effects has historically been associated with chronic use of classic cyclooxygenase inhibitors, all of which are about equipotent for COX-1 or COX-2, or which are COX-1-selective. While renal toxicity occurs, it usually becomes evident in patients who already exhibit renal insufficiency (D. Kleinknecht, Sem. Nephrol. 15: 228, 1995). By far, the most prevalent and morbid toxicity is gastrointestinal. Even with relatively nontoxic drugs such as piroxicam, up to 4% of patients experience gross bleeding and ulceration (M. J. S. Langman et al, Lancet 343: 1075, 1994). In the United States, it is estimated that some 2000 patients with rheumatoid arthritis and 20,000 patients with osteoarthritis die each year due to gastrointestinal side effects related to the use of COX inhibitors. In the UK, about 30% of the annual 4000 peptic ulcer-related deaths are attributable to COX inhibitors (Scrip 2162, p.17). COX inhibitors cause gastrointestinal and renal toxicity due to the inhibition of synthesis of homeostatic prostaglandins responsible for epithelial mucus production and renal blood flow, respectively.

The second form of cyclooxygenase, COX-2, is rapidly and readily inducible by a number of agents including mitogens, endotoxins, hormones, cytokines and growth factors. It has been proposed that COX-2 is mainly responsible for the pathological effects of prostaglandins, which arise when rapid induction of COX-2 occurs in response to such agents as inflammatory agents, hormones, growth factors, and cytokines. Selective inhibitors of COX-2 have anti-inflammatory, antipyretic and analgesic properties similar to those of a conventional non-steroidal anti-inflammatory drug (NSAID), but COX-2 inhibitors have been touted as providing a reduced potential for gastrointestinal toxicity, among other side effects. Nevertheless, experience with selective COX-2 inhibitors is limited relative to experience with non-selective COX inhibitors (which non-selectively inhibit COX-1 and COX-2). Non-selective COX inhibitors are widely used, and it is expected that these drugs will continue to be widely used. Further, there has been recent suggestions that COX-2 inhibitors have serious but previously unrecognized side effects, including increased intraocular pressure and the risk of glaucoma, as well as possible effects on the central nervous system.

For years, neutralization of gastric acid with antacids was the only relief from the pain of ulcers. However, more recently, a class of antisecretory agents that do not exhibit anticholinergic or $H_2$ histamine antagonistic properties, but that suppress gastric acid secretion by the specific inhibition of the $H^+$, $K^+$—ATPase enzyme system at the secretory surface of the gastric parietal cell, has been developed. These agents (hereinafter "proton pump inhibitors") provide a more specific class of inhibitors of gastric acid secretion in mammals and man by blocking the final step of acid production.

Generally, proton pump inhibitors, their single enantiomers or alkaline salts thereof, are used for the prevention and treatment of gastric acid related diseases including, but not limited to, reflux esophagitis, gastritis, duodenitis, gastric ulcer and duodenal ulcer. These proton pump inhibitors may also be used in patients in intensive care situations, in patients with acute upper gastrointestinal bleeding, pre- and postoperatively to prevent acid aspiration of gastric acid and to prevent and treat stress ulceration. Also, they may be useful in the treatment of psoriasis as well as in the treatment of Helicobacter infections and diseases related to these. Additionally, these proton pump inhibitors may be used for the treatment of other gastrointestinal disorders where gastric acid inhibitory effect is desirable, such as patients with Non Ulcer Dyspepsia, in patients with symptomatic gastroesophageal reflux disease, in patients with gastrinomas, and in particular in patients on NSAID therapy.

U.S. Pat. No. 5,817,338 (Bergstrand, et al.) describes multiple unit tableted dosage forms of omeprazole, a proton pump inhibitor commercially available for inhibiting gastric acid secretion in humans. Therein, it is suggested that omeprazole may be used for treatment of other gastrointestinal disorders where gastric acid inhibitory effect is desirable, e.g., in patients on NSAID therapy. However, this patent does not describe pharmaceutical formulations combining a proton pump inhibitor such as omeprazole with an NSAID.

SUMMARY OF THE INVENTION

It is an object of this invention to provide a method for the treatment of pain, inflammation, and/or fever with the use of a NSAID without the undesirable stomach discomfort and other side effects typically associated with NSAID therapy.

It is a further object of the invention to decrease the risk of the development and/or exacerbation of ulcers which may occur during NSAID therapy.

It is a further object of the invention to promote patient compliance and thereby increase efficacy of NSAID treatment in patients who are being chronically treated with NSAIDs.

It is a further object of the invention to provide prophylactic treatment to a human patient who is on NSAID therapy or is about to begin NSAID therapy, in order to avoid or minimize gastrointestinal side-effects.

It is a further object of the invention to provide prophylactic treatment to a human patient who is on a therapy known to have significant gastrointestinal side effects or is about to begin such a therapy, in order to avoid or minimize such side effects.

It is a further object of the invention to provide cost effective therapy to decrease the risk of the development and/or exacerbation of ulcers which may occur during NSAID therapy.

In view of the above-mentioned objects and others, the invention is directed to an oral solid dosage form comprising a therapeutically effective amount of an NSAID and a proton pump inhibitor in an amount effective to inhibit or prevent gastrointestinal side effects normally associated with the NSAID treatment.

The invention is further directed to a solid oral dosage form comprising
   a) an NSAID (e.g. diclofenac or a pharmaceutically acceptable salt thereof) extended release tablet and
   b) an enterically coated proton-pump inhibitor without a separating layer between the proton pump inhibitor and the enteric coat.

The invention is further directed to a (non-steroidal) antiinflammatory, analgesic, and antipyretic oral therapy which does not possess any substantial gastrointestinal side-effects, comprising an orally administrable dosage form comprising a therapeutically effective amount of an NSAID and an amount of a proton pump inhibitor effective to substantially inhibit gastrointestinal side effects of the NSAID, together with one or more pharmaceutically acceptable excipients.

The invention is further directed to a dosage form comprising a therapeutically effective amount of an NSAID and an amount of a proton pump inhibitor effective to substantially inhibit gastrointestinal side effects of the NSAID, wherein said proton pump inhibitor is coated with a material suitable to prevent contact of said proton pump inhibitor with acidic gastric juice (e.g. an enteric coating). In preferred embodiments, the material is directly coated onto the proton pump inhibitor without a separating layer between the material and the proton pump inhibitor.

The invention is further directed to the prophylactic treatment of a human patient who is on NSAID therapy or is about to begin NSAID therapy, via the concurrent administration of a proton pump inhibitor.

The invention is further directed to the prophylactic treatment of a human patient who is on a therapy known to have significant gastrointestinal side effects or is about to begin such a therapy, via the concurrent administration of a proton pump inhibitor.

The invention is further related to a method of treating a human patient in need of antiinflammatory, analgesic and/or antipyretic therapy, comprising orally administering to the patient an oral pharmaceutical dosage form comprising a therapeutically effective amount of an NSAID and an amount of a proton pump inhibitor effective to substantially inhibit gastrointestinal side effects of the NSAID.

In certain preferred embodiments, the dosage form is an oral tablet comprising the NSAID, the proton pump inhibitor, and one or more pharmaceutically acceptable excipients. In other preferred embodiments, the NSAID and the proton pump inhibitor comprise a mixture of tablets, powders, pellets, granules, or inert nonpareil beads coated with the drugs, contained within a gelatin capsule.

The inventive formulations and methods described herein promote patient compliance and thereby increase efficacy of NSAID treatment in patients who are being chronically treated with NSAIDs. In other words, the inventive formulations increase the likelihood that a patient on NSAID therapy who is noncompliant due to gastrointestinal side effects, or who forgets or refuses to take both medications separately will be more accepting of a single composition combining the NSAID and proton pump inhibitor, particularly due to the avoidance of gastrointestinal side effects.

Proton pump inhibitors are known to be highly acid labile, and therefore it is preferred that the proton pump inhibitor(s) contained in the dosage forms of the invention be protected from contact with acidic gastric juice.

In certain preferred embodiments, the proton pump inhibitor is omeprazole.

In certain preferred embodiments, the NSAID is diclofenac, more preferably diclofenac sodium.

For purposes of this disclosure, all references to proton pump inhibitors and NSAIDs include their single enantiomers and their pharmaceutically acceptable salts.

For purposes of this disclosure, the phrase "substrates" is meant to encompass inert pharmaceutically acceptable beads, particles, granules or pellets.

For purposes of this disclosure, the phrase "combination pharmaceutical" shall be understood to include any drug composition containing at least two therapeutically active components of which at least one is a non-steroidal antiinflammatory drug. The term "pain-alleviating" shall be understood herein to include the expressions "pain-suppressing" and "pain-inhibiting" as the invention is applicable to the alleviation of existing pain as well as the suppression or inhibition of pain which would otherwise ensue from an imminent pain-causing event.

DETAILED DESCRIPTION OF THE INVENTION

The term "NSAID," as used herein, refers to any compound acting as a non-steroidal anti-inflammatory agent identifiable as such by one of ordinary skill in the art. For many years NSAIDs have been used for treating pain and/or inflammation. "Treating" includes prophylaxis of a physical and/or mental condition or amelioration or elimination of the developed condition once it has been established, or alleviation of the characteristic symptoms of such condition. The term "pain" includes all types of pain. Pain includes, but is not limited to, chronic pains, such as arthritis pain (e.g. pain associated with osteoarthritis and rheumatoid arthritis), neuropathic pain, and post-operative pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, migraine, angina pain, and genitourinary tract-related pain including cystitis, the term also refers to nociceptive pain or nociception.

The Merck Manual, 16th Edition, Merck Research Laboratories (1990) pp 1308–1309 provide well known examples of NSAIDs. The term NSAID includes, but is not limited to, the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, ketoprofen, meclofenamic acid, mefenamic acid, niflumic acid, phenacetin, salidifamides, sulindac, suprofen and tolmetin. The salicylates may include acetylsalicylic acid, sodium acetylsalicylic acid, calcium acetylsalicylic acid, salicylic acid, and sodium salicylate.

NSAIDs have been widely used in arthritis therapy for several years. The following references, hereby incorporated by reference, describe various NSAIDs suitable for use in the invention described herein, and processes for their manufacture: U.S. Pat. No. 3,558,690 to Sallmann and Pfister, (assigned to Ciba Geigy), issued 1971; U.S. Pat. No. 3,843,681 (assigned to American Home Products), issued 1974; U.S. Pat. No. 3,766,263 to Godfrey, (assigned to Reckitt and Colman) issued 1973; U.S. Pat. No. 3,845,215 to Godfrey (assigned to Reckitt and Colman) issued 1974; U.S. Pat. No. 3,600,437 to Marshall (assigned to Eli Lilly), issued 1971; U.S. Pat. No. 3,228,831 to Nicholson and Adams, (assigned to Boots Pure Drug), issued 1966; (U.S. Pat. No. 3,385,886 to Nicholson and Adams, (assigned to Boots Pure Drug) issued 1968; U.S. Pat. No. 3,161,654 to Shen, (assigned to Merck & Co.), issued 1964; U.S. Pat. No. 3,904,682 to Fried and Harrison, (assigned to Syntex), issued 1975; U.S. Pat. No. 4,009,197 to Fried and Harrison, (assigned to Syntex), issued 1977; U.S. Pat. No. 3,591,584 to Lombardino (assigned to Pfizer) issued 1971; U.S. Pat. No. 5,068,458 to Dales et al., (assigned to Beecham Group, PLC.), issued Nov. 26, 1991; U.S. Pat. No. 5,008,283 to Blackbum et al. (assigned to Pfizer, Inc.), issued Apr. 16, 1991; and U.S. Pat. No. 5,006,547 to Loose (assigned to Pfizer), issued Apr. 9, 1991. All of the above patents are hereby incorporated by reference.

Proton pump inhibitors (PPI) are potent inhibitors of gastric acid secretion, inhibiting $H^+$, $K^+$—ATPase, the enzyme involved in the final step of hydrogen ion production in the parietal cells. The term proton pump inhibitor includes, but is not limited to, omeprazole, lansoprazole, rabeprazole, pantoprazole and leminoprazole, including isomers, enantiomers and tautomers thereof, and alkaline salts thereof Proton pump inhibitors typically include benzimidazole compounds. The following patents describe various benzimidazole compounds suitable for use in the invention described herein: U.S. Pat. No. 4,045,563, U.S. Pat. No. 4,255,431, U.S. Pat. No. 4,359,465, U.S. Pat. No. 4,472,409, U.S. Pat. No. 4,508,905, JP-A-59181277, U.S. Pat. No. 4,628,098, U.S. Pat. No. 4,738,975, U.S. Pat. No. 5,045,321, U.S. Pat. No. 4,786,505, U.S. Pat. No. 4,853,230, U.S. Pat. No. 5,045,552, EP-A-295603, U.S. Pat. No. 5,312,824, EP-A-166287, EP-A-519365, EP5129, EP 174,726, EP 166, 287 and GB 2,163,747. All of the above patents are hereby incorporated by reference. Proton pump inhibitors, e.g. omeprazole and its pharmaceutically acceptable salts, which are used in accordance with the invention are known compounds and can be produced by known processes. In certain preferred embodiments, the proton pump inhibitor is omeprazole, either in racemic mixture or only the (−) enantiomer of omeprazole (i.e. esomeprazole), as set forth in U.S. Pat. No. 5,877,192, hereby incorporated by reference.

Omeprazole is typically administered in a 20 mg dose/day for active duodenal ulcer for 4–8 weeks; in a 20 mg dose/day for gastro-esophageal reflux disease (GERD) or severe erosive esophagitis for 4–8 weeks; in a 20 mg dose/twice a day for treatment of Helicobacter pylori (in combination with other agents); in a 60 mg dose/day for active duodenal ulcer for 4–8 weeks and up to 120 mg three times/day; and in a 40 mg dose/day for gastric ulcer for 4–8 weeks. Such dosages are contemplated to be within the scope of the invention. Thus, in certain embodiments of the invention, the amount of proton pump inhibitor which is included in the dosage form is an amount which is considered to be therapeutically effective, in accordance with the dosages set forth above for a variety of disease states. In other preferred embodiments of the invention, the dose of proton pump inhibitor is sub-therapeutic. For example, when the drug is omeprazole, the dosage form may contain from about 0.1 mg to about 120 mg omeprazole.

Lansoprazole is typically administered about 15–30 mg/day, rabeprazole is typically administered 20 mg/day and pantoprazole is typically administered 40 mg/day. However, any therapeutic or sub-therapeutic dose of these agents is considered within the scope of the present invention.

The proton pump inhibitor(s) included in the dosage forms of the invention are preferably protected from contact with acidic gastric juice, and preferably is transferred without exposure to gastric fluid until the dosage form reaches a part of the gastrointestinal tract where the pH is near neutral and where rapid absorption of omeprazole can occur.

In preferred embodiments of the invention, the pharmaceutical compositions containing the proton pump inhibitors and NSAIDs set forth herein are administered orally. Such oral dosage forms may contain one or both of the drugs in immediate or sustained release form. The oral dosage forms may be in the form of tablets, capsules, troches, lozenges, aqueous or oily suspensions, dispersible powders or granules, emulsions, multiparticulate formulations, syrups, elixirs, and the like.

The combination of proton pump inhibitor and a NSAID can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Aqueous suspensions containing the above-identified combination of drugs and that mixture have one or more excipients suitable as suspending agents, for example pharmaceutically acceptable synthetic gums such as hydroxypropyhnethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed.

As is well known in the art, proton pump inhibitors are susceptible to degradation and/or transformation in acidic and neutral media. For example, the half-life of degradation of omeprazole in water solutions at pH-values less than three is shorter than ten minutes. The degradation of proton pump inhibitors is catalyzed by acidic compounds and is stabilized in mixtures with alkaline compounds. The stability of this class of antisecretory compounds is also affected by moisture, heat, organic solvents and to some degree by light. With respect to the stability properties of the proton pump inhibitors, it is preferable that in an oral solid dosage form they be protected from contact with the acidic gastric juice and the active substance must be transferred in intact form to that part of the gastrointestinal tract where pH is near neutral and where rapid absorption of the medication can occur. Formulations which address the degradation of proton pump inhibitors in acidic media are described in U.S. Pat. Nos. 4,786,505, 5,817,338; and 5,798,120, each of which is hereby incorporated by reference, and each of the described formulations in those patents can be modified to include one or more NSAIDs pursuant to the present invention.

One preferred embodiment of the invention is a combination pharmaceutical composition having two active ingredients, comprising a proton pump inhibitor and a NSAID in a single composition, in which the proton pump inhibitor is in the form of individually enteric coated substrates' layered onto an NSAID tablet. The enteric coating layer(s) covering the substrates of the proton pump inhibitor (with or without the NSAID) is preferably sufficient to provide acid resistance to the substrates. Preferably, the enteric coating layer covering the substrates disintegrates/dissolves rapidly in near neutral or alkaline media.

In formulations prepared using multiparticulate substrates comprising enterically coated proton pump inhibitor, such multiparticulates may be mixed with NSAID (e.g., in particulate or powder form) and then separated into unit doses. Alternatively, the enterically coated substrates containing the proton pump inhibitor may thereafter by coated with the NSAID (with or without further optional overcoatings are described in more detail below). Alternatively, two separate populations of substrates may be used, one population of substrates being coated with the proton pump inhibitor and thereafter enteric-coated, the other population of substrates comprising the NSAID. The NSAID-containing substrates may comprise inert beads coated with the NSAID, or may comprise a plurality of immediate release matrices containing the NSAID. Thereafter, requisite amounts of each of the two populations of substrates could be incorporated into tablets, or into gelatin capsules, for example.

In embodiments where the substrates comprise inert pharmaceutically acceptable beads, the drug(s) may be mixed with further ingredients prior to being coated onto the beads. Ingredients include, but are not limited to, binders, surfactants, fillers, disintegrating agents, alkaline additives or other pharmaceutically acceptable ingredients, alone or in mixtures. Binders include, for example, celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants include pharmaceutically acceptable non-ionic or ionic surfactants. An example of a suitable surfactant is sodium lauryl sulfate. The inert beads may be first coated with the proton pump inhibitor, overcoated with an enteric coating, and thereafter coated with the NSAID (with or without further optional overcoatings are described in more detail below). Alternatively, two separate populations of beads may be used, one population of beads being coated with the proton pump inhibitor and thereafter enteric-coated, the other population of beads being coating with the NSAID. Thereafter, requisite amounts of each of the two populations of beads could be incorporated into tablets, or into gelatin capsules, for example.

Alternatively, the proton pump inhibitor may be optionally mixed with alkaline compounds and further mixed with suitable ingredients (with or without the NSAID) as set forth above and then formulated into the substrate. Such substrates may be manufactured via extrusion/spheronization, balling or compression utilizing different process equipments. The size of the substrates may be, for example, from about 0.1 to about 4 mm, and preferably from about 0.1 to about 2 mm. Alternatively, the substrates may include additional ingredients, optionally comprising the NSAID. Such suitable ingredients include fillers, binders, lubricants, disintegrating agents, surfactants and other pharmaceutically acceptable additives. The alkaline compound may be selected from substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminum, calcium and magnesium hydroxides; magnesium oxide or composite substances, such as $Al_2O_3.6MgO.CO_2 12H_2O$, $(Mg_6Al_2 (OH)_{16} CO_3.4H_2O)$, $MgO.Al_2O_3.2SiO_2.nH_2O$ or similar compounds; organic pH-buffering substances such as trihydroxymethylaminomethane, basic amino acids and their salts or other similar, pharmaceutically acceptable pH-buffering substances.

Alternatively, the aforementioned substrate can be prepared by using spray drying or spray congealing technique.

The proton pump inhibitor omeprazole has an asymmetric centre in the sulfur atom, i.e. exists as two optical isomers (enantiomers). Both the pure enantiomers, racemic mixtures (50% of each enantiomer) and unequal mixtures of the two enantiomers are suitable for the pharmaceutical formulation according to the present invention. A suitable form of omeprazole for preparation of multiparticulate dosage forms in accordance with the invention can be the magnesium salt of omeprazole with a specific degree of crystallinity and other physical properties disclosed in WO 95/01977, hereby incorporated by reference. Other suitable forms of the active substance are the sodium, potassium, magnesium and calcium salts of the single enantiomers of omeprazole, especially in their crystalline form described in WO 94/27988, hereby incorporated by reference.

Before applying enteric coating layer(s) onto the substrate, the substrates may optionally be covered with one or more separating (intermediate) layers, however, in preferred embodiments, the enteric coating is applied directly onto the proton pump inhibitor without the need for a separating layer.

Preferably, one or more enteric coating layers are applied onto the substrate using a suitable coating technique. The enteric coating layer material may be dispersed or dissolved in either water or in suitable organic solvents. As enteric coating layer polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s).

The enteric coating layers preferably contain effective amounts of pharmaceutically acceptable plasticizers to obtain the desired mechanical properties, such as flexibility and hardness of the enteric coating layers. Such plasticizers are for instance, but not restricted to, triacetin, citric acid esters, phthalic acid esters, dibutyl sebacate, cetyl alcohol, polyethylene glycols, polysorbates or other plasticizers. The amount of plasticizer is optimized for the particular situation. The amount of plasticizer is usually above 10% by weight of the enteric coating layer polymer(s), preferably 15–50%, and more preferably 20–50%. Additives such as dispersants, colorants, pigments, polymers e.g. poly (ethylacrylate, methylmethacrylate), anti-tacking and anti-foaming agents may also be included into the enteric coating layer(s). Other compounds may be added to increase film thickness and to decrease diffusion of acidic gastric juices into the add susceptible material.

Overcoatings may be applied to the substrates coated as set forth above, e.g., by coating or layering procedures in suitable equipments such as coating pan, coating granulator or in a fluidized bed apparatus using water and/or organic solvents for the coating or layering process. Suitable overcoating materials include sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and the like. Additives such as plasticizers, colorants, pigments, fillers, anti-tacking and anti-static agents, such as for instance magnesium stearate, titanium dioxide, talc and other additives may also be included into the over-coating layer(s).

The enteric coated substrates may then be mixed with tablet excipients (and with the NSAID in certain embodiments) and compressed into a multiple unit tableted dosage form according to the present invention, or alternatively incorporated as unit doses in appropriately sized gelatin capsules. Compressed tablets prepared in accordance with the invention are optionally covered with a film-forming agent(s) to obtain a smooth surface of the tablet and further enhance the stability of the tablet during packaging and transport. Such a tablet coating layer may further comprise additives like anti-tacking agents, colorants and pigments or other additives to obtain a tablet of good appearance. The compaction process (compression) for formulating the multiple unit tableted dosage form must not significantly affect the acid resistance of the enteric coated substrates. In other words the mechanical properties, such as the flexibility and hardness as well as the thickness, of the enteric coating layer(s) must secure that the requirements on enteric coated articles in the United States Pharmacopeia are accomplished and that the acid resistance does not decrease more than 10%, during the compression of pellets into tablets.

In certain preferred embodiments, where the NSAID is incorporated into the formulation after the enteric coating of the proton pump inhibitor substrates, the addition of the NSAID after the addition of the enteric coating to the substrates allows for rapid release of the NSAID and delayed release of proton pump inhibitor. The NSAID may be present in an outer coating in a form that does not retard its release, or may be separately incorporated into the formulation as set forth above.

Optionally soft gelatin capsules can be manufactured by filling a composition comprising the active ingredients as mentioned above and a known vegetable oil into capsules. Hard gelatin capsules can also be manufactured by filling into capsules the tablet, granules or pellets, each comprising an active ingredient as mentioned above, and a solid particulate carrier such as lactose, sucrose, sorbitol, mannitol, potato starch, corn starch, amylopectin, a cellulose derivative or gelatin.

It is often considered desirable to administer NSAIDs in sustained release form in order to reduce the number of NSAID doses per day, thereby improving patient compliance and efficacy. Proton pump inhibitors are generally administered on a once- or twice-a-day basis, and it has not generally been contemplated to incorporated proton pump inhibitors into a sustained release dosage form. The details of how to achieve slowing or delaying of the release are familiar to the skilled worker on the basis of his expert knowledge. The skilled worker is likewise familiar with suitable ancillary substances and vehicles for the required dosage forms (pharmaceutical formulations). Besides solvent, tablet auxiliary substances and other active ingredient excipients it is possible to use, for example, tablet-coating compositions, plasticizers, antioxidants, preservatives, and dyes. Where incompatibilities between the active ingredients or between the active ingredients and ancillary substances are expected, suitable separating layers are provided where appropriate (for example in layered or multi-layer tablets).

In certain embodiments in which the NSAID is incorporated into the dosage form in a sustained release form designed to slowly release the NSAID over time, the proton pump inhibitor may be formulated in the dosage form to release via a different mechanism, e.g., via an enteric coating. However, in view of the rationale for administration of the proton pump inhibitors in accordance with the invention (prophylaxis as opposed to treatment of existing disease states), it is contemplated that in certain preferred embodiments, the proton pump inhibitor is incorporated into the dosage form in a sustained release state together with the NSAID.

In certain embodiments, the NSAID (and optionally the proton pump inhibitor) can be formulated as a sustained release oral formulation in any suitable tablet, coated tablet or multiparticulate formulation known to those skilled in the art. The sustained release dosage form may optionally include a sustained released carrier which is incorporated into a matrix along with the drug(s), or the sustained release carrier can be applied as a sustained release coating. The sustained release dosage form may comprise a plurality of substrates which include the NSAID and/or the NSAID and the proton pump inhibitor. The substrates may comprise matrix spheroids or may comprise inert pharmaceutically acceptable beads which are coated with the drug(s). The coated beads may then be overcoated with a sustained release coating comprising the sustained release carrier. The matrix spheroid may include the sustained release carrier in the matrix itself; or the matrix may comprise a normal release matrix containing the drugs, the matrix having a coating applied thereon which comprises the sustained release carrier. In yet other embodiments, the oral solid dosage form comprises a tablet core containing the drugs within a normal release matrix, with the tablet core being coated with a sustained release coating comprising the sustained release carrier. In yet further embodiments, the tablet contains the drugs within a sustained release matrix comprising the sustained release carrier. In yet further embodiments, the tablet contains the NSAID within a sustained release matrix and the proton pump inhibitor coated into the tablet in an enteric coated layer. In yet further embodiments, the dosage form comprises a plurality of multiparticulates comprising the NSAID in sustained release form (e.g., prepared in any of the manners set forth above) together with a population of a plurality of multiparticulates comprising the proton pump inhibitor in an acid-protected form (e.g., enteric coated).

The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the proton pump inhibitor in desired areas of the gastro-intestinal (GI) tract, e.g., the small intestine, such that an absorption profile is provided which is capable of providing at least about twelve hour and preferably up to twenty-four hour relief to a patient. When a pH-independent coating is desired, the coating is designed to achieve optimal release regardless of pH-changes in the environmental fluid, e.g., the GI tract. It is also possible and preferable to formulate compositions which release a portion of the dose, preferably the NSAID, in one desired area of the GI tract, e.g., the stomach, and release the remainder of the dose, preferably the proton pump inhibitor, in another area of the GI tract, e.g., the small intestine.

Formulations according to the invention that utilize pH-dependent coatings to obtain formulations may also impart a repeat-action effect whereby unprotected drug, preferably the NSAID, is coated over the enteric coat and is released in the stomach, while the remainder, preferably containing the proton pump inhibitor, being protected by the enteric coating, is released further down the gastrointestinal tract. Coatings which are pH-dependent may be used in accordance with the present invention, including shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the proton pump inhibitor (with or without the NSAD) is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile.

In certain preferred embodiments, the oral dosage form of the present invention comprises a compressed matrix comprising the NSAID or a salt thereof and a retardant material in an effective amount to provide a controlled release of the NSAID for at least about 24 hours; a proton pump inhibitor coated on the surface of the matrix, wherein the proton pump inhibitor is in an amount effective to inhibit gastrointestinal side effects normally associated with oral administration of the NSAID; and an overcoat with a material suitable to prevent contact of said proton pump inhibitor with acidic gastric juice after oral administration. Preferably, the NSAID is diclofenac or a pharmaceutically acceptable salt thereof and the proton pump inhibitor is omeprazole or a pharmaceutically acceptable salt thereof.

The retardant material which may be included in the matrix with the NSAID can include one or more pharmaceutically acceptable hydrophobic materials and/or hydrophilic materials which are capable of imparting controlled release of the active agent in accordance with the present invention.

The hydrophobic material is preferably selected from the group consisting of waxes, alkylcelluloses, acrylic and methacrylic acid polymers and copolymers, hydrogenated castor oil, hydrogenated vegetable oil, gums, protein derived materials, aliphatic alcohols or mixtures thereof.

In certain embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material is selected from materials such as alkylcelluloses, e.g. methylcellulose or ethylcellulose. In other embodiments, the hydrophobic material is an aliphatic alcohol, e.g. lauryl alcohol, myristyl alcohol, or stearyl alcohol.

An example of a suitable retardant material having hydrophilic properties is a hydroxyalkylcellulose, e.g. hydroxypropylmethylcellulose.

This list is not meant to be exclusive, and any pharmaceutically acceptable hydrophobic material and/or hydrophilic material which are capable of imparting controlled release of the active agent may be used in accordance with the present invention.

In addition to the above ingredients, the matrix may also contain suitable quantities of other materials, e.g. diluents, lubricants, binders, granulating aids, colorants, flavorants and glidants that are conventional in the pharmaceutical art. The quantities of these additional materials will be sufficient to provide the desired effect to the desired formulation. Specific examples of pharmaceutically acceptable carriers and excipients that may be used to formulate oral dosage forms are described in the *Handbook of Pharmaceutical Excipients*, American Pharmaceutical Association (1986), incorporated by reference herein.

A further ingredient which can be added to the matrix is a pH modifying agent which is defined for purposes of the present invention to mean any substance which decreases the ionization of the medicament, whereby the release of the drug from the matrix and into solution is facilitated. Suitable pH modifying agent are organic acids such as citric acid, succinic acid, fumaric acid, malic acid, maleic acid, glutaric acid or lactic acid.

Prior to coating the matrix with the proton pump inhibitor, the matrix can be coated with a pharmaceutically acceptable film-coating, e.g., for stability purposes (e.g., coated with a moisture barrier), etc. For example, the matrix may be overcoated with a film coating, preferably containing a pigment and a barrier agent, such as hydroxypropylmethylcellulose and/or a polymethylmethacrylate. An example of a suitable material which may be used for such a hydrophilic coating is hydroxypropylmethylcellulose (e.g., Opadry®, commercially available from Colorcon, West Point, Pa.). Any pharmaceutically acceptable manner known to those skilled in the art may be used to apply the coatings. For example, the coating may be applied using a coating pan or a fluidized bed. An organic, aqueous or a mixture of an organic and aqueous solvent is used for the hydrophobic polymer or enteric coating. Examples of suitable organic solvents are, e.g., isopropyl alcohol, ethanol, and the like, with or without water. Aqueous solvents are preferred for the overcoating procedures.

The proton pump inhibitor is coated onto the tablet. Preferably, a solution of the proton pump inhibitor is spray dried onto the surface of the tablet using any spray technique known to those skilled in the art. This coating can also be applied using a coating pan or a fluidized bed using an organic, aqueous or a mixture of an organic and aqueous solvent for the proton pump inhibitor. Preferably, aqueous solvents are preferred for the proton pump inhibitor coating.

The material suitable to prevent contact of said proton pump inhibitor with acidic gastric juice after oral administration is then overcoated onto the proton pump inhibitor coated matrix. This material preferably contains an enteric polymer. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example is sold under the trademark Eudragit™ L 100-555. as defined above. This coating can be spray coated onto the substrate as previously mentioned with respect to the other layers of this embodiment of the invention. Preferably, the coating to prevent contact of said proton pump inhibitor with acidic gastric juice is applied directly over the proton pump inhibitor without an intermediate separating layer.

In another preferred embodiment of the invention, the oral solid dosage form comprises a compressed matrix comprising (i) an NSAID or a salt thereof and a retardant material in an effective amount to provide a controlled release of the NSAID for at least about 24 hours and (ii) a plurality of particles comprising a proton pump inhibitor in a sufficient amount to provide an effective dose of the proton pump inhibitor to inhibit or prevent gastrointestinal side effects associated with diclofenac treatment. Preferably, the NSAID is diclofenac or a pharmaceutically acceptable salt thereof and the proton pump inhibitor is omeprazole or a pharmaceutically acceptable salt thereof.

The compressed matrix of this embodiment can be prepared in accordance with the compressed matrix described in the immediately preceding embodiment. For example, the retardant material can be an aliphatic alcohol, such as a stearyl alcohol and can be combined with the NSAID to form a matrix.

The plurality of particles comprising the proton pump inhibitor can be in the form of substrates coated with the proton pump inhibitor and then overcoated with a material suitable to prevent contact of said proton pump inhibitor with acidic gastric juice after oral administration, e.g. an enteric coating. Preferably, the coating to prevent contact of said proton pump inhibitor with acidic gastric juice is applied directly over the proton pump inhibitor without an intermediate separating layer.

In embodiments where the substrates comprise a plurality of inert pharmaceutically acceptable beads, the proton pump inhibitor can be mixed with further ingredients prior to being coated onto the beads. Ingredients include, but are not limited to, binders, surfactants, fillers, disintegrating agents, alkaline additives or other pharmaceutically acceptable ingredients, alone or in mixtures. Binders include, for example, celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants include pharmaceutically acceptable non-ionic or ionic surfactants. An example of a suitable surfactant is Polysorbate-80.

The NSAID matrix and the proton pump inhibitor particles are then encapsulated in a pharmaceutically acceptable capsule.

In embodiments where the NSAID is included in sustained release form, the amount of NSAID included will generally be based upon a multiple of the amount administered in immediate release form, depending of course upon the dosage frequency. In general, when the proton pump inhibitor is incorporated in sustained release form as well as the NSAID, the amount of proton pump inhibitor will remain within the same limits as set forth above with respect to enteric release forms.

DETAILED DESCRIPTION OF CERTAIN PREFERRED EMBODIMENTS

The following examples illustrate various aspects of the present invention. They are not to be construed to limit the claims in any manner whatsoever.

EXAMPLE 1

Preparation of Diclofenac sodium Extended-release/ Omeprazole Delayed-release Tablets, 100/20 mg The above formulation was prepared by preparing diclofenac extended release (ER) granules and compressing the granules into tablets. The tablets are were seal coated, followed by spray coating with an omeprazole suspension. The omeprazole coated tablet was then enteric coated, followed by a color coating.

In particular, the ingredients as set forth below in Table 1 were granulated to form Diclofenac Sodium ER Granules:

TABLE 1

| Ingredients | % Weight |
| --- | --- |
| Diclofenac Sodium, USP | 45.87 |
| Fumaric Acid, NF | 1.01 |
| Cetyl Alcohol, NF | 6.01 |
| Stearyl Alcohol, NF | 6.01 |
| Colloidal Silicon Dioxide (CAB-O-SIL M-5) | 1.01 |
| Compressible Sugar (DI-PAC) | 40.09 |
| Total | 100.00 |

The Diclofenac Sodium granules were then compressed with Magnesium Stearate to form Diclofenac Sodium ER Tablets, 100 mg (Uncoated). These uncoated tablets were then seal coated and drug layered with the ingredients set forth in Table 2.

TABLE 2

| Ingredients | % Weight |
| --- | --- |
| Diclofenac Sodium ER Tablets, 100 mg (uncoated) | 78.596 |
| Omeprazole, USP (micronized) | 8.217 |
| Opadry Clear YS-1-7006 | 2.858 |
| L-Arginine Base, USP/FCC | 0.146 |

TABLE 2-continued

| Ingredients | % Weight |
| --- | --- |
| Polysorbate 80, NF | 0.733 |
| D-Mannitol, USP | 8.217 |
| Povidone, USP | 1.233 |
| Purified Water, USP* | * |
| Total | 100.000 |

*Evaporate during the process

For the seal coating, the Opadry Clear was added to the Purified Water, USP and sprayed onto the uncoated tablets. After a 10 minute drying period, an omeprazole suspension with the remaining ingredients were sprayed onto the seal coated tablets to form an immediate release (IR) omeprazole layer.

The Diclofenac Sodium ER/Omeprazole IR tablets, 100/20 mg were then enteric coated with the ingredients set forth in Table 3. The enteric coating was applied directly onto the immediate release omeprazole layer without an intermediate separating layer.

TABLE 3

| Ingredients | % Weight |
| --- | --- |
| Diclofenac Sodium ER/Omeprazole DR Tablets | 90.462 |
| Hydroxypropyl Methylcellulose Phthalate 50, NF | 4.637 |
| Talc, USP | 4.637 |
| Cetyl Alcohol, NF | 0.265 |
| Isopropyl Alcohol, USP* | * |
| Acetone, NF* | * |
| Total | 100.000 |

*Evaporated during the coating process

These enteric coated tablets were then color coated with an aqueous solution of Opadry White to form the final product.

Figure 1:
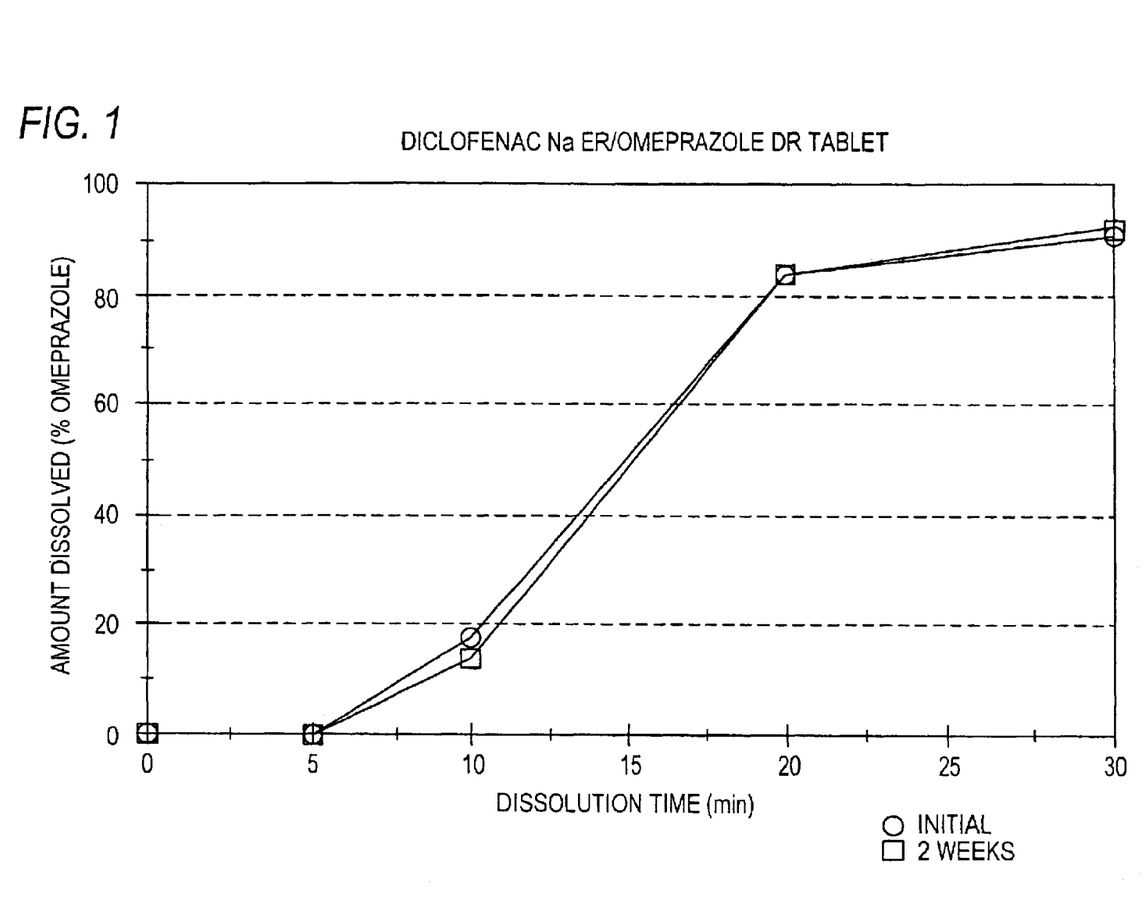
FIG. 1 is a graph of in vitro dissolution data which shows the dissolution profile of omeprazole from the initial formulation of Example 1 and the formulation of Example 1 after exposure to accelerated storage conditions of 40° C. and 75% relative humidity for 2 weeks. The dissolution medium is a 0.5 M Phosphate buffer at a pH 6.8.

The dissolution profile of omeprazole from the Diclofenac Sodium ER/Omeprazole DR tablets in a 0.5 M Phosphate buffer medium at a pH 6.8 is set forth in FIG. 1 and Table 4 below:

TABLE 4

| | Amount Dissolved (% Omeprazole) | | | | | | | | | |
| --- | --- | --- | --- | --- | --- | --- | --- | --- | --- | --- |
| Time (min) | V1 | V2 | V3 | V4 | V5 | V6 | Mean | % RSD | Min. | Max |
| 0 | 0 | 0 | 0 | 0 | 0 | 0 | 0 | 0 | 0 | 0 |
| 5 | 0 | 0 | 0 | 0 | 0 | 1 | 0 | 245 | 0 | 1 |
| 10 | 13 | 16 | 13 | 22 | 25 | 20 | 18 | 27 | 13 | 25 |
| 20 | 86 | 89 | 81 | 82 | 81 | 88 | 85 | 4 | 81 | 89 |
| 30 | 92 | 93 | 92 | 90 | 86 | 95 | 91 | 3 | 86 | 95 |

Figure 2:
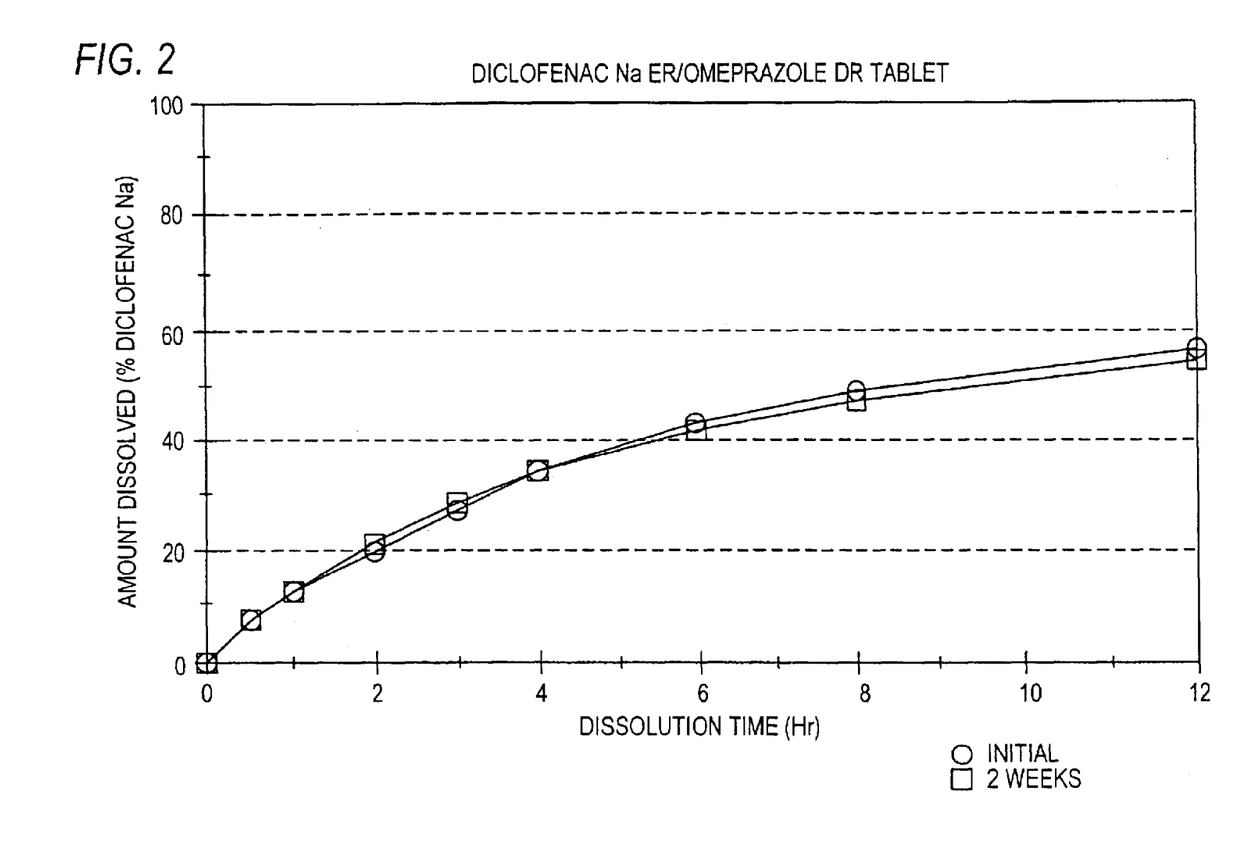
FIG. 2 is a graph of in vitro dissolution data which shows the dissolution profile of diclofenac from the initial formulation of Example 1 and the formulation of Example 1 after exposure to accelerated storage conditions of 40° C. and 75% relative humidity for 2 weeks. The dissolution medium is a 0.5 M Phosphate buffer at a pH 6.8.

The dissolution profile of diclofenac from the Diclofenac Sodium ER/Omeprazole DR tablets in a 0.5 M Phosphate buffer medium at a pH 6.8 is set forth in FIG. 2 and Table 5 below:

TABLE 5

| | Amount Dissolved (% Diclofenac sodium) | | | | | | | | | |
| --- | --- | --- | --- | --- | --- | --- | --- | --- | --- | --- |
| Time (Hr) | V1 | V2 | V3 | V4 | V5 | V6 | Mean | % RSD | Min. | Max |
| 0 | 0 | 0 | 0 | 0 | 0 | 0 | 0 | 0 | 0 | 0 |
| 0.5 | 7 | 7 | 7 | 7 | 7 | 7 | 7 | 4 | 7 | 7 |

TABLE 5-continued

Amount Dissolved (% Diclofenac sodium)

| Time (Hr) | V1 | V2 | V3 | V4 | V5 | V6 | Mean | % RSD | Min. | Max |
|---|---|---|---|---|---|---|---|---|---|---|
| 1 | 12 | 12 | 12 | 12 | 12 | 12 | 12 | 3 | 12 | 12 |
| 2 | 20 | 20 | 20 | 20 | 21 | 21 | 20 | 3 | 20 | 21 |
| 3 | 27 | 27 | 27 | 27 | 28 | 28 | 27 | 2 | 27 | 28 |
| 4 | 33 | 34 | 34 | 35 | 35 | 34 | 34 | 2 | 33 | 35 |
| 6 | 43 | 43 | 44 | 45 | 45 | 44 | 44 | 2 | 43 | 45 |
| 8 | 49 | 49 | 50 | 51 | 50 | 50 | 50 | 2 | 49 | 51 |
| 12 | 56 | 56 | 57 | 59 | 56 | 57 | 57 | 2 | 56 | 59 |

The tablets were then exposed to accelerated storage conditions of 40° C. and 75% relative humidity for 2 weeks. The dissolution of omeprazole and diclofenac from the accelerated storage tablets in a 0.5 M Phosphate buffer medium at a pH 6.8 showed the formulation to be stable.

EXAMPLE 2

Preparation of Diclofenac sodium ER/Omeprazole DR Capsules, 100/20 mg

The above formulation was prepared by preparing diclofenac extended release granules and compressing the granules into tablets, followed by a seal coating. Delayed release enteric coated omeprazole pellets were then prepared and encapsulated with the extended release diclofenac tablet.

In particular, Diclofenac Sodium ER Tablets, 100 mg (Seal Coated) tablets were prepared in accordance with Example 1.

Omeprazole Active Pellets were prepared by coating inert beads with an omeprazole suspension in accordance with the ingredients set forth-in Table 6 below:

TABLE 6

| Ingredients | % Weight |
|---|---|
| Sugar Sphere, NF (18/20) | 69.700 |
| Omeprazole, USP (micronized) | 14.000 |
| Polysorbate 80, NF | 1.250 |
| L-Arginine Base, USP | 0.250 |
| D-Mannitol, USP | 14.000 |
| Povidone, USP (Plasdone K-90) | 0.800 |
| Purified Water, USP* | * |
| Total | 100.000 |

*Evaporated during the coating process

The omeprazole active pellets were then enteric coated with the ingredients set forth in Table 7. The enteric coating was applied directly on to the omeprazole pellets without an intermediate separating layer.

TABLE 7

| Ingredients | % Weight |
|---|---|
| Omeprazole Active Pellets | 81.00 |
| Hydroxypropyl Methylcellulose Phthalate 55, NF | 9.27 |
| Cetyl Alcohol, NF | 0.46 |
| Talc, USP | 9.27 |
| Isopropyl Alcohol, USP* | * |
| Acetone, NF* | * |
| Total | 100.00 |

*Evaporated during the process

A sufficient amount of enteric coated omeprazole pellets to provide 20 mg omeprazole were then encapsulated with a Diclofenac Sodium ER seal coated tablet to form Diclofenac Sodium ER/Omeprazole DR Capsules, 100/20 mg.

Figure 3:
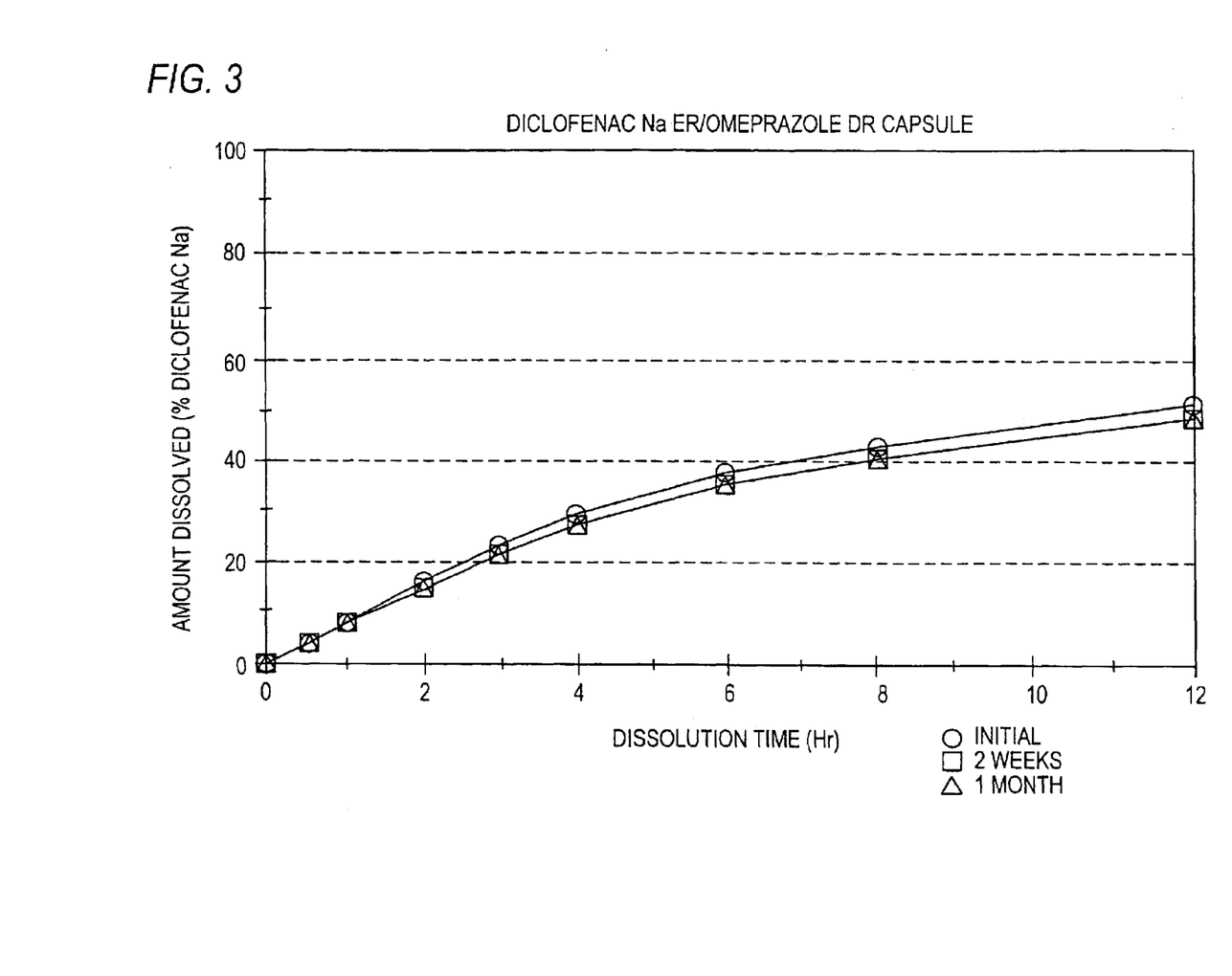
FIG. 3 is a graph of in vitro dissolution data which shows the dissolution profile of diclofenac from the initial formulation of Example 2, the formulation of Example 2 after exposure to accelerated storage conditions of 40° C. and 75% relative humidity for 2 weeks and the formulation of Example 2 after exposure to accelerated storage conditions of 40° C. and 75% relative humidity for 1 month. The dissolution medium is a 0.5 M Phosphate buffer at a pH 6.8.

The dissolution profile of diclofenac from the Diclofenac Sodium ER/Omeprazole DR capsules in a 0.5 M Phosphate buffer medium at a pH 6.8 is set forth in FIG. 3 and Table 8 below:

TABLE 8

Amount Dissolved (% Diclofenac sodium)

| Time (Hr) | V1 | V2 | V3 | V4 | V5 | V6 | Mean | % RSD | Min | Max |
|---|---|---|---|---|---|---|---|---|---|---|
| 0 | 0 | 0 | 0 | 0 | 0 | 0 | 0 | 0 | 0 | 0 |
| 0.5 | 4 | 4 | 4 | 4 | 3 | 4 | 4 | 3 | 3 | 4 |
| 1 | 7 | 8 | 8 | 8 | 7 | 8 | 8 | 2 | 7 | 8 |
| 2 | 15 | 16 | 16 | 15 | 15 | 16 | 16 | 2 | 15 | 16 |
| 3 | 23 | 23 | 22 | 22 | 23 | 24 | 23 | 2 | 22 | 24 |
| 4 | 29 | 29 | 28 | 28 | 28 | 30 | 29 | 3 | 28 | 30 |
| 6 | 38 | 38 | 36 | 36 | 36 | 38 | 37 | 3 | 36 | 38 |
| 8 | 44 | 43 | 42 | 42 | 42 | 44 | 43 | 3 | 42 | 44 |
| 12 | 52 | 51 | 49 | 49 | 49 | 52 | 50 | 3 | 49 | 52 |

Figure 4:
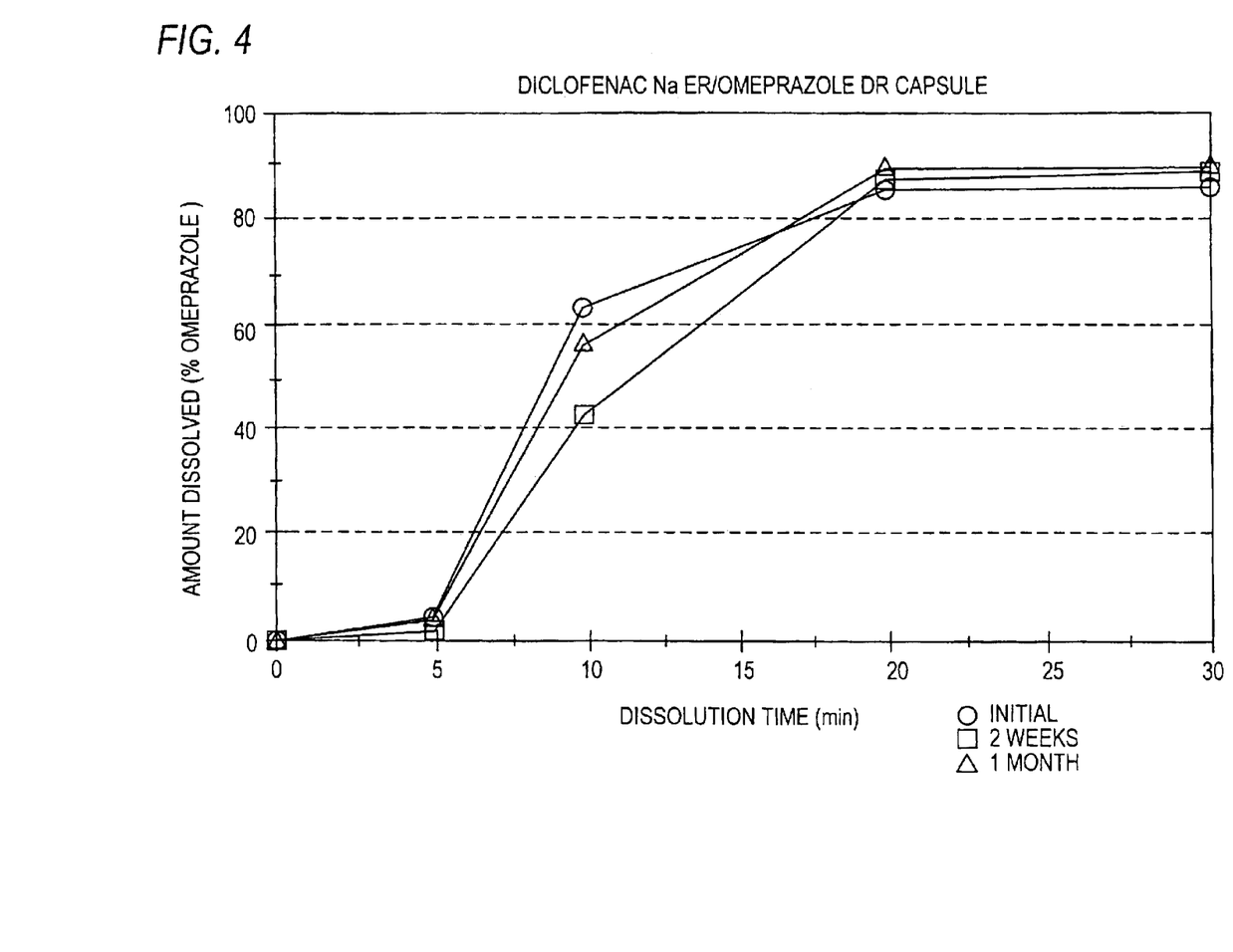
FIG. 4 is a graph of in vitro dissolution data which shows the dissolution profile of omeprazole from the initial formulation of Example 2, the formulation of Example 2 after exposure to accelerated storage conditions of 40° C. and 75% relative humidity for 2 weeks and the formulation of Example 2 after exposure to accelerated storage conditions of 40° C. and 75% relative humidity for 1 month. The dissolution medium is a 0.5 M Phosphate buffer at a pH 6.8.

The dissolution profile of omeprazole from the Diclofenac Sodium ER/Omeprazole DR capsules in a 0.5 M Phosphate buffer medium at a pH 6.8 is set forth in FIG. 4 and Table 9 below:

TABLE 9

Amount Dissolved (% Omeprazole)

| Time (min) | V1 | V2 | V3 | V4 | V5 | V6 | Mean | % RSD | Min. | Max |
|---|---|---|---|---|---|---|---|---|---|---|
| 0 | 0 | 0 | 0 | 0 | 0 | 0 | 0 | 0 | 0 | 0 |
| 5 | 3 | 3 | 5 | 6 | 4 | 10 | 5 | 50 | 3 | 10 |
| 10 | 59 | 58 | 66 | 71 | 55 | 71 | 64 | 11 | 55 | 71 |
| 20 | 86 | 86 | 87 | 89 | 82 | 88 | 86 | 3 | 82 | 89 |
| 30 | 87 | 87 | 86 | 89 | 82 | 88 | 87 | 3 | 82 | 89 |

Capsules were then exposed to accelerated storage conditions of 40° C. and 75% relative humidity for 2 weeks. The dissolution of diclofenac from the accelerated storage capsules in a 0.5 M Phosphate buffer medium at a pH 6.8 showed the formulation to be stable.

EXAMPLES 3–7

In Example 3, Diclofenac Sodium ER Tablets are prepared and seal coated in accordance with Example 1. These seal coated tablets are then sprayed with an aqueous lansoprazole solution or suspension and enteric coated in accordance with the drug layering and enteric coating procedures of Example 1. The final dosage form contains 100 mg diclofenac sodium and 15 mg lansoprazole.

In Example 4, Diclofenac Sodium ER Tablets are prepared and seal coated in accordance with Example 1. These seal coated tablets are then sprayed with an aqueous pantoprazole solution or suspension and enteric coated in accordance with the drug layering and enteric coating procedures of Example 1. The final dosage form contains 100 mg diclofenac sodium and 40 mg pantoprazole.

In Example 5, Diclofenac Sodium ER Tablets are prepared and seal coated in accordance with Example 1. These seal coated tablets are then sprayed with an aqueous rabeprazole solution or suspension and enteric coated in accordance with the drug layering and enteric coating procedures of Example 1. The final dosage form contains 100 mg diclofenac sodium and 20 mg rabeprazole.

In Example 6, Diclofenac Sodium ER Tablets are prepared and seal coated in accordance with Example 1. These seal coated tablets are then sprayed with an aqueous esomeprazole solution or suspension and enteric coated in accordance with the drug layering and enteric coating procedures of Example 1. The final dosage form contains 100 mg diclofenac sodium and 20 mg esomeprazole.

In Example 7, Diclofenac Sodium ER Tablets are prepared and seal coated in accordance with Example 1. These seal coated tablets are then sprayed with an aqueous (+) omeprazole solution or suspension and enteric coated in accordance with the drug layering and enteric coating procedures of Example 1. The final dosage form contains 100 mg diclofenac sodium and 20 mg (+) omeprazole.

EXAMPLE 8–12

In Example 8, Diclofenac Sodium ER Tablets are prepared and seal coated in accordance with Example 2. Lansoprazole Active Pellets are prepared and enteric coated in accordance with the bead layering and enteric coating procedures of Example 2. A sufficient amount of enteric coated pellets to provide 15 mg lansoprazole are then encapsulated with the Diclofenac Sodium ER seal coated tablet to form Diclofenac Sodium ER/Lansoprazole DR Capsules, 100/15 mg.

In Example 9, Diclofenac Sodium ER Tablets are prepared and seal coated in accordance with Example 2. Pantoprazole Active Pellets are prepared and enteric coated in accordance with the bead layering and enteric coating procedures of Example 2. A sufficient amount of enteric coated pellets to provide 40 mg pantoprazole are then encapsulated with the Diclofenac Sodium ER seal coated tablet to form Diclofenac Sodium ER/Pantoprazole DR Capsules, 100/40 mg.

In Example 10, Diclofenac Sodium ER Tablets are prepared and seal coated in accordance with Example 2. Rabeprazole Active Pellets are prepared and enteric coated in accordance with the bead layering and enteric coating procedures of Example 2. A sufficient amount of enteric coated pellets to provide 20 mg rabeprazole are then encapsulated with the Diclofenac Sodium ER seal coated tablet to form Diclofenac Sodium ER/Rabeprazole DR Capsules, 100/20 mg.

In Example 11, Diclofenac Sodium ER Tablets are prepared and seal coated in accordance with Example 2. Esomeprazole Active Pellets are prepared and enteric coated in accordance with the bead layering and enteric coating procedures of Example 2. A sufficient amount of enteric coated pellets to provide 20 mg esomeprazole are then encapsulated with the Diclofenac Sodium ER seal coated tablet to form Diclofenac Sodium ER/Esomeprazole DR Capsules, 100/20 mg.

In Example 12, Diclofenac Sodium ER Tablets are prepared and seal coated in accordance with Example 2. (+) Omeprazole Active Pellets are prepared and enteric coated in accordance with the bead layering and enteric coating procedures of Example 2. A sufficient amount of enteric coated pellets to provide 20 mg (+) omeprazole are then encapsulated with the Diclofenac Sodium ER seal coated tablet to form Diclofenac Sodium ER/(+) omeprazole DR Capsules, 100/20 mg.

In Examples 1 and 2, the specified proton pump inhibitor is in the arginine salt form. Equivalent amounts of other forms of the proton pump inhibitor such as the free base, pharmaceutically acceptable salts thereof (e.g., the sodium, potassium, magnesium, calcium and amino acid salts, or mixtures thereof) or mixtures thereof, can be utilized as well.

What is claimed is:

1. A solid oral dosage form comprising
   a) a population of substrates comprising a proton-pump inhibitor;
   b) an enteric coating layer coated over said substrates; and
   c) an NSAID coating layer coated over said enteric coated substrates.

2. The solid oral dosage form of claim 1 further comprising a film coating over said NSAID coating.

3. The solid dosage form of claim 1 further comprising a film coating over said enteric coat.

4. The solid dosage form of claim 1 wherein said proton pump inhibitor is selected from the group consisting of omeprazole, lansoprazole, rabeprazole, pantoprazole, leminoprazole, single enantiomers thereof, alkaline salts thereof and mixtures thereof.

5. The solid dosage form of claim 1 wherein said proton pump inhibitor is omeprazole or a pharmaceutically acceptable salt thereof.

6. The solid dosage form of claim 1 wherein said substrates are a plurality of inert beads and said proton-pump inhibitor is coated onto said beads.

7. The solid dosage form of claim 1 wherein said solid oral dosage form is a capsule which contains a sufficient amount of said substrates to provide a therapeutic effect.

8. The solid dosage form of claim 7 wherein said proton pump inhibitor is selected from the group consisting of omeprazole, lansoprazole, rabeprazole, pantoprazole, leminoprazole, single enantiomers thereof, alkaline salts thereof and mixtures thereof.

9. The solid dosage form of claim 8 wherein said proton pump inhibitor is omeprazole or a pharmaceutically acceptable salt thereof.

10. A solid dosage form for oral administration comprising a compressed matrix comprising an NSAID and a proton-pump inhibitor, and a retardant material in an effective amount to provide a controlled release of said NSAID and said proton-pump inhibitor sufficient to provide a therapeutic effect for at least about 24 hours; and said compressed matrix overcoated with a material suitable to prevent contact of said proton pump inhibitor with acidic gastric juice after oral administration.

11. The solid dosage form of claim 10 wherein said proton pump inhibitor is selected from the group consisting of omeprazole, lansoprazole, rabeprazole, pantoprazole, leminoprazole, single enantiomers thereof, alkaline salts thereof and mixtures thereof.

12. The solid dosage form of claim 11 wherein said proton pump inhibitor is omeprazole or an alkaline salt thereof.

13. The solid dosage form of claim 10, wherein said proton pump inhibitor is in an amount effective to inhibit gastrointestinal side effects associated with oral administration of said NSAID or pharmaceutically acceptable salt thereof.

14. The solid dosage form of claim 10 wherein said material suitable to prevent contact of said proton pump inhibitor with acidic gastric juice is an enteric coating.

15. The solid dosage form of claim 14 comprising a film coating or color coating over said enteric coating.

16. The solid dosage form of claim 10 wherein said retardant material is an aliphatic alcohol.

17. The solid dosage form of claim 16 wherein said aliphatic alcohol is selected from the group consisting of stearyl alcohol, cetyl alcohol and mixtures thereof.

18. The solid dosage form of claim 10 wherein said NSAID, said proton-pump inhibitor and said retardant material are in granular form prior to compression.

19. The oral dosage form of claim 14, wherein said enteric coating comprises a methacrylic acid copolymer, cellulose acetate phthalate, hydroxypropylmethylcellulose phthalate, hydroxypropyl methylcellulose acetate succinate, polyvinyl acetate phthalate, cellulose acetate trimellitate, carboxymethylethylcellulose, or shellac.

20. A solid dosage form for oral administration comprising
    a compressed matrix tablet comprising an NSAID and a retardant material in an effective amount to provide a controlled release of said NSAID; and
    a plurality of particles comprising a proton pump inhibitor coated onto the surface of a plurality of inert beads and overcoated with a material suitable to prevent contact of said proton pump inhibitor with acidic gastric juice after oral administration; paid dosage form containing a sufficient amount of said particles to provide an effective dose of said proton pump inhibitor to inhibit gastrointestinal side effects associated with oral administration of said NSAID;
    said compressed matrix and said dose of proton pump inhibitor contained within a capsule.

21. The oral solid dosage form of claim 20, wherein said proton-pump inhibitor is selected from the group consisting of omeprazole, lansoprazole, rabeprazole, pantoprazole, leminoprazole, single enantiomers thereof, alkaline salts thereof and mixtures thereof.

22. The solid oral dosage form of claim 1, wherein the proton-pump inhibitor is in a therapeutically effective amount.

23. The solid oral dosage form of claim 1, wherein the proton-pump inhibitor is in an amount effective to inhibit gastrointestinal side effects associated with oral administration of said diclofenac or pharmaceutically acceptable salt thereof.

24. The solid oral dosage form of claim 1, wherein the NSAID is selected from the group consisting of indomethacin, flurbiprofen, diclofenac, naproxen, piroxicam, tebufelone, ibuprofen, etodolac, nabumetone, tenidap, alcofenac, antipyrine, aminopyrine, dipyrone, aminopyrone, phenylbutazone, clofezone oxyphenbutazone, prexazone, apazone, benzydamine, bucolome, cinchopen, clonixin, ditrazol, epirizole, fenoprofen, floctafeninl, flufenamic acid, glaphenine, indoprofen, ketoprofen, meclofenamic acid, mefenamic acid, niflumic acid, phenacetin, sulindac, suprofen, tolmetin, pharmaceutically acceptable salts thereof and mixtures thereof.

25. The solid oral dosage form of claim 10, wherein the NSAID is selected from the group consisting of indomethacin, flurbiprofen, diclofenac, naproxen, piroxicam, tebufelone, ibuprofen, etodolac, nabumetone, tenidap, alcofenac, antipyrine, aminopyrine, dipyrone, aminopyrone, phenylbutazone, clofezone oxyphenbutazone, prexazone, apazone, benzydamine, bucolome, cinchopen, clonixin, ditrazol, epirizole, fenoprofen, floctafeninl, flufenamic, glaphenine, indoprofen, ketoprofen, meclofenamic acid, mefenamic acid, niflumic acid, phenacetin, sulindac, suprofen, tolmetin, pharmaceutically acceptable salts thereof and mixtures thereof.

26. The solid oral dosage form of claim 20, wherein the NSAID is selected from the group consisting of indomethacin, flurbiprofen, diclofenac, naproxen, piroxicam, tebufelone, ibuprofen, etodolac, nabumetone, tenidap, alcofenac, antipyrine, aminopyrine, dipyrone, aminopyrone, phenylbutazone, clofezone oxyphenbutazone, prexazone, apazone, benzydamine, bucolome, cinchopen, clonixin, ditrazol, epirizole, fenoprofen, floctafeninl, flufenamic acid, glaphenine, indoprofen, ketoprofen, meclofenamic acid, mefenamic acid, niflumic acid, phenacetin, sulindac, suprofen, tolmetin, pharmaceutically acceptable salts thereof and mixtures thereof.

* * * * *